United States Patent [19]

Atrash et al.

[11] Patent Number: 5,424,291
[45] Date of Patent: Jun. 13, 1995

[54] ISOSTERIC PEPTIDES

[76] Inventors: Butrus Atrash, 2 Meon Crescent, Chandlers Ford, Hampshire SO5 2PB; David M. Jones, 'Sundew', Slab Lane, West Wellow, Hampshire SO51 6BY; Michael Szelke, 'Southview', Braishfield, Romsey, Hampshire SO51 OPN, all of Great Britain

[21] Appl. No.: 288,657

[22] Filed: Aug. 10, 1994

Related U.S. Application Data

[63] Continuation of Ser. No. 751,700, Aug. 29, 1991, abandoned.

[30] Foreign Application Priority Data

Aug. 28, 1991 [SE] Sweden ............................. 9102462

[51] Int. Cl.$^6$ ...................... A61K 37/02; C07K 5/08
[52] U.S. Cl. ..................................... 514/18; 514/822; 530/331
[58] Field of Search .................. 514/18, 822; 530/331

[56] References Cited

U.S. PATENT DOCUMENTS 4,318,904 3/1982 Shaw et al. .

FOREIGN PATENT DOCUMENTS 0118280 9/1984 European Pat. Off. .
0192135 8/1986 European Pat. Off. .
0479489 4/1992 European Pat. Off. .

OTHER PUBLICATIONS

Yang et al. Biochem J. 272(2), 399–406 (1990).

*Primary Examiner*—Jill Warden
*Assistant Examiner*—Benet Prickril

[57] ABSTRACT

Compounds of formula I relate to the peptide sequence of human fibrogen A$\alpha$ chain, with modified positions 14 through 17 ($P_3$–$P_1^1$), which may be a useful inhibitor of thrombin. The antithrombin and anticoagulant compounds of this invention, therefore, have therapeutic potential in treatment or prophylaxis of thrombosis and related atherosclerotic diseases. A procedure for the synthesis of peptides according to formula I is also described.

14 Claims, 1 Drawing Sheet

Fig. 1

ISOSTERIC PEPTIDES

This application is a continuation of application Ser. No. 07/751,700, filed on Aug. 29, 1991, now abandoned.

DESCRIPTION

This invention relates to new competitive inhibitors of thrombin, their synthesis, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial infarction and cerebral thrombosis, general hypercoagulable states and local hypercoagulable states, e.g. following angioplasty and coronary bypass operations.

1. Background

Figure 1:
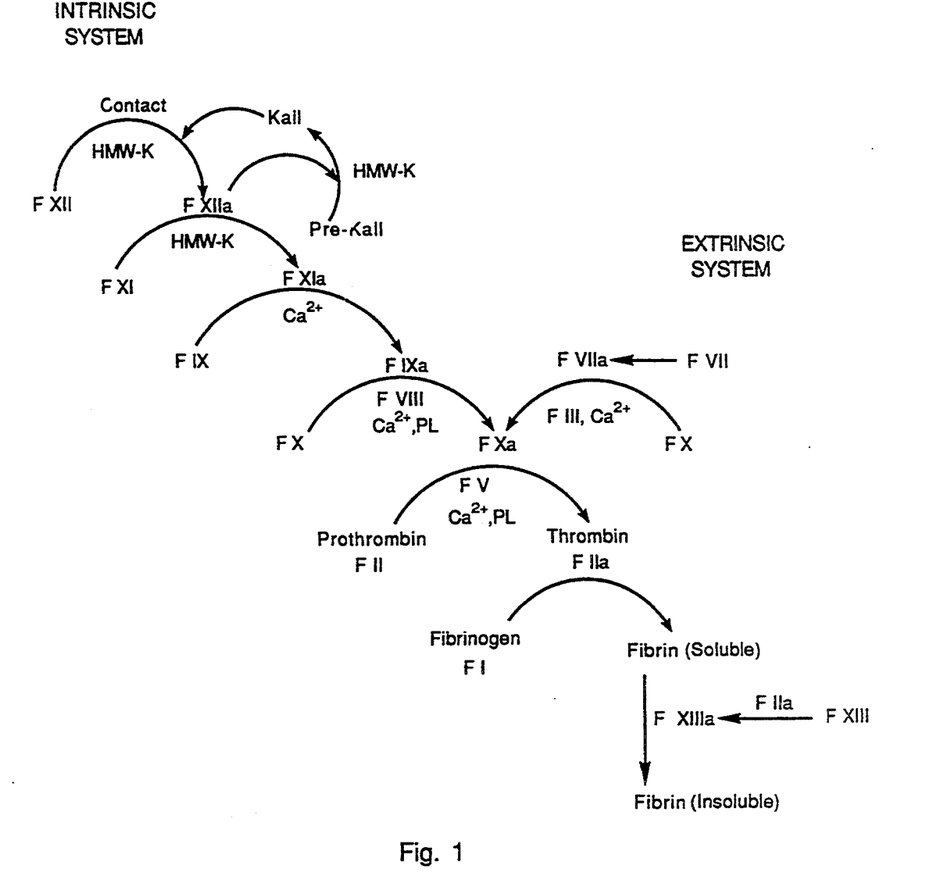
FIG. 1 depicts the intrinsic and extrinsic cascade pathways leading to blood coagulation.

Blood coagulation is the key process involved in both haemostasis (i.e. prevention of blood loss from a damaged vessel) and thrombosis (i.e. the pathological occlusion of a blood vessel by a blood clot). Coagulation is the result of a complex series of enzymatic reactions outlined in FIG. 1 where the various clotting factors are designated by Roman numerals.

Thrombin plays a central role in coagulation, whether the process is initiated by the intrinsic or extrinsic pathways: it activates platelets, it converts fibrinogen into fibrin monomers, which polymerise spontaneously into filaments, and it activates FXIII, which in turn cross-links the polymer to insoluble fibrin. Thrombin further activates FV and FVIII in a positive feedback reaction. Inhibitors of thrombin are therefore expected to be effective anticoagulants.

2. Prior Art

The first inhibitors of thrombin based on electrophilic ketones were developed as described by M. Szelke and D. M. Jones in EP-A1-0,118,280, GB priority date 4th Mar. 1983. These earlier compounds were derived from the $P_3$-$P_2'$ pentapeptide sequence of the fibrinogen A$\alpha$ chain in which the scissile $P_1$-$P_1'$ peptide bond was replaced with the —CO—CH$_2$—moiety, forming a keto isostere to the corresponding peptides.

Other known examples of serine proteinase inhibitors based on electrophilic ketones include the following:

(a) M. Kolb et al. (Merrel-Dow) EP-A2-0,195,212 (Priority date 4 Feb. 1986) describing peptidic α-keto esters and amides, (b) B. Imperiali and R. H. Abeles, Biochemistry 1986. 25. 3760 (peptidyl fluoroalkyl ketones), (c) Ueda et al., Biochem. J. 1990. 265. 539 (peptidyl fluoroalkyl ketones).

(d) D. Schirlin et al. (Merrel-Dow) EP-A1-0,362,002 (priority date 1 Sep. 1988) describing fluoroalkylamide ketones.

(e) P. Bey et al. (Merrel-Dow) EP-A2-0,364,344 (priority date 7 Oct. 1988) describing α, β, δ-triketo compounds.

(f) E. N. Shaw et al. (Research Corporation) U.S. Pat. No. 4,318,904, (priority date 25 Apr. 1980) describing peptide chloro-methyl ketones e.g. H-DPhe-Pro-Arg-CH$_2$Cl Inhibitors of thrombin based on peptide aldehydes have been reported by S. Bajusz et al. in J. Med. Chem. 1990. 33. 1729, and in (Richter Gedeon Vegyeszeti Gyar R. T.) EP-A2-0,185,390 (priority date 21 Dec. 1984).

Thrombin inhibitors as peptides comprising C-terminal boronic acid derivatives of arginine and isothiouronium analogues thereof have been reported by A. D. Kettner et al. (Du Pont) EP-A2-0,293,881 (priority dates 5 Jun. 1987 and 6 Apr. 1988).

There are examples of thrombin inhibitory arginine derivatives or analogues not containing an electrophilic ketone, e.g.:

(a) S. Okamoto et al. (Mitsubishi Chemical Industries Ltd.) EP-A1-0,008,746 (priority date 31 Aug. 1978) describing arylsulphonyl arginine amides e.g. argatroban.

(b) J. Stürzebecher et al., Pharmazie 1981. 36. 639 (arylsulphonyl p-amidinophenylalanine amides).

An object of the present invention is to provide novel and potent thrombin inhibitors with competitive inhibitory activity towards their enzyme i.e. causing reversible inhibition. A further object is to obtain inhibitors which are orally bioavailable and selective in inhibiting thrombin over other serine proteases. Stability, duration of action, and low toxicity at therapeutic dosages are still further objects of the invention.

DISCLOSURE OF THE INVENTION

Compounds

It has been found that compounds of the general formula 1, either as such or in the form of physiologically acceptable salts and including stereoisomers, are potent inhibitors of thrombin:

In formula 1, and when occurring below unless specified otherwise, the following applies:

A represents —CH$_2$—, —CH=CH—, —CH$_2$—CH$_2$— or —CH$_2$—CH$_2$—CH$_2$—;

$R^1$ and $R^2$ are the same or different and each represents H or X—B—, where B is a straight or branched alkylene group having 1–3 carbon atoms and X is H, methyl, ethyl, a cycloalkyl group having 3–6 carbon atoms or R'CO—, where R' is OH, a straight or branched alkoxy group having 1–4 carbon atoms, NH$_2$ or NHR'', where R'' is a straight or branched alkyl group having 1–4 carbon atoms, or X is a carboxylic acid mimic, known per se, selected from —PO(OR''')$_2$, —SO$_3$H and 5-(1H)-tetrazolyl, and R''' is H, methyl or ethyl, or B is —SO$_2$— and X is methyl or ethyl;

m is 0, 1 or 2, $R^3$ represents a cyclohexyl group and $R^{3,4}$ represents H; or m is 1 and $R^3$ represents a cyclohexyl or phenyl group and $R^{3,4}$ forms an ethylene bridge together with $R^1$;

Y represents O or S(O)$_p$, where p is 0, 1 or 2;

$R^4$ represents H; a straight or branched alkyl or a cycloalkyl having 1 to 6 carbon atoms unsubstituted or substituted with one or more fluoro atoms and/or substituted with a phenyl group; a substituted or unsubstituted aromatic ring selected from phenyl, 4-methoxy-phenyl, 4-tertiary-butyl-phenyl, 4-methyl-phenyl, 2-, 3- or 4-trifluoro-methyl-phenyl, phenyl substituted with 1–5 fluoro atoms; or —CH(CF$_3$)-phenyl.

Compounds of formula 1 relate to the peptide sequence of human fibrinogen Aα chain representing modified sub-sites P$_3$-P$_1$':

This sequence is identified as SEQ ID NO: 1 in the Sequence Listing.

According to a preferred embodiment the invention relates to compounds of Formula 1, wherein A represents —CH$_2$—CH$_2$— or —CH$_2$—CH$_2$—CH$_2$—;

R$^1$ is H and R$^2$ represents HOCO(CH$_2$)$_n$— or CH$_3$CH$_2$OCO(CH$_2$)$_n$—, and n is 1 or 2;

Y is O m is 1, R$^3$ represents a cyclohexyl group and R$^{3A}$ represents H;

Particularly advantageous embodiments of the invention are represented by the compounds:

HOOC—CH$_2$-DCha-Pro-Arg-CH$_2$—O—CH$_2$—CF$_3$
HOOC—CH$_2$-DCha-Pic-Arg-CH$_2$—O—CH$_2$—CF$_3$
HOOC—CH$_2$-DCha-Pic-Arg-CH$_2$—O-nBu
HOOC—CH$_2$—CH$_2$-DCha-Pro-Arg-CH$_2$—O-nBu
HOOC—CH$_2$—CH$_2$-DCha-Pro-Arg-CH$_2$—O—CH$_2$—CF$_3$
HOOC—CH$_2$-DCha-Pro-Arg-CH$_2$—O-nBu

Medical and pharmaceutical use

In a further embodiment the invention relates to treatment, in a human or animal organism, of conditions where inhibition of thrombin is required. The compounds of the invention are expected to be useful in particular in animals including man in treatment or prophylaxis of thrombosis and hypercoagulability in blood and tissues. Disease states in which the compounds have a potential utility, in treatment and/or prophylaxis, include venous thrombosis and pulmonary embolism, arterial thrombosis, such as in myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in prophylaxis for re-occlusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anti-coagulant treatment in haemodialysis and disseminated intravascular coagulation. The daily dosage will normally be within 0.1 mg to 10 g of active ingredient. Intravenous solutions preferably contain 0.1–100 mg/ml, while a dosage unit preferably contains 1–1000 mg and is preferably administered 1–4 times a day.

A further expected utility is in rinsing of catheters and mechanical devises used in patients in vivo, and as an anticoagulant for preservation of blood, plasma and other blood products in vitro.

Preparation

A further objective of the invention is the mode of preparation of the compounds of the invention. Thus the invention further relates to a process for preparation of compounds according to formula 1, which process comprises (method I) displacement by R$^4$Y— (Y=O,S) of the halogen of a halomethylketone of the formula wherein W$^1$ is an amino terminal protecting group such as tertiary butoxycarbonyl and W$^2$ is a protecting group such as benzyloxy carbonyl, (as illustrated in Procedures (A), (D) and (F)), reduction of the ketone to alcohol, removal of the amino terminal protecting group, standard peptide coupling, followed by oxidation of the alcohol, giving the protected tripeptide ketone, removal of the amino terminal protecting group, followed by N-alkylation, (as illustrated in Procedures (A), (B), (G) and (H)), and deprotection, or replacing a protected dipeptide in the coupling reaction referred to above and-illustrated (e.g. Procedure (A)(iii)), with an amino-terminal-N-alkylated-N-trifluoroacyl-protected dipeptide (Procedure K), followed by oxidation and deprotection, or (method II) alkylation, with an R$^4$-halide, of an α-ketol of the formula wherein W$^1$ and W$^2$ are as defined above, (as illustrated in Procedure (E)), and then further reacting as in method I, or (method III) by using the modified Dakin-West reaction, Angew. Chem. Int. Ed. Engl. 8 (1969) 981, as applied to tripeptides, J. Org. Chem., 50 (1985)1112: reacting a compound of the formula (or alternatively to directly use an amino-terminal-N-alkylated-N-trifluoroacyl-protected tripeptide)

wherein W[1] and W[2] are as defined above, with (T—CH$_2$CO)$_2$O wherein T is halogen, R[4]O or R[4]S and 4-DMAP, and then further reacting as in method I.

In those cases where the reaction results in a mixture of stereoisomers, these are optionally separated by standard chromatographic or re-crystallisation techniques, and if desired a single stereoisomer is isolated.

DETAILED DESCRIPTION OF THE INVENTION

The following description is illustrative of aspects of the invention.

Synthesis and pharmacy

The chemistry used to prepare the inhibitors claimed here is outlined in the Synthesis schemes (Procedures A to H) and Procedures I and K. The necessary alkoxy- or phenoxymethyl ketones of arginine were mainly prepared by (I) displacement by R[4]O— of the Br of bromomethylketones, either using preformed NaOR[4] (Procedure A) or by the use of KF (Procedures D and F) or (II) by alkylation of arginine α-ketol using Ag$_2$O/R[4]I (see Procedure E).

Standard peptide coupling reactions were used to introduce Dcha, Pro and their analogues. The carboxyalkyl group on the N-terminus was introduced either by alkylation using bromo-acetates or by Michael addition to tertiary butylacrylate (Procedures A, B)—or by using pre-incorporation of carboxy-alkyl in the dipeptide moiety (see Procedure K). All protecting groups were then removed (see Deprotection Procedures a–c below).

General experimental procedures:

Standard work-up refers to ethyl acetate extractions, usually washing with 0.3M KHSO$_4$, 1M KHCO$_3$, H$_2$O and brine followed by filtration through Whatman Phase Separatory paper and drying by toluene azeotroping. TLC was carried out on commercial Merck Silicagel 60F254 coated glass plates. Visualization was by a combination of UV light, heating followed by fluorescamine spray or heating followed by chlorination (Cl$_2$ tank) and spraying with 1% starch/KI solution. Flash chromatography was carried out on Merck Silicagel 60 (40–63 μm) under pressure of N$_2$. Amino acid analysis was performed using the Beckman Gold System. Peptides were hydrolysed (6N HCl+phenol at 110° C. for 22 h) then injected and the proline peak quantified. MPLC was carried out in glass columns (Anachem) packed with Vydac C18 15–25 μm silica, using gradients of 1% TFA-MeCN into 1% TFA-H$_2$O with monitoring at 226 nm. Fractions were analyzed by HPLC and the pure ones pooled and lyophilised. HPLC was carried out using a Spectra-Physics 8700 Series chromatography station. Solvent system as for MPLC with detection at 210 nm. Flow 1.5 ml/min. Column: Novapak C18, 4 μm (8×100 mm cartridge, Waters). All intermediates were characterised by NMR (Hitachi-Perkin Elmer R24 60 MHz or Jeol 270 MHz instruments). All final peptides were characterised by their FAB mass spectra (M-Scan Ascot, Berks., U.K.).

Preparation of starting materials:

Boc-Arg(Z$_2$)—CH$_2$Br (i) Boc-Arg(Z$_2$)—OH (10 mmol) in dry THF (50 ml) and NMM (10 mmol) was cooled to −10° C. and iBC (10 mmol) added dropwise keeping the temp. ≦−10° C. After 10 min at −10° C. the mixed anhydride was poured into CH$_2$N$_2$-ether (25 mmol in 150 ml). After 3 h excess CH$_2$N$_2$ was destroyed with acetic acid and the solution washed with H$_2$O (3×) and brine. Drying and evaporation gave the diazoketone as a yellow oil. IR 2100 cm−1 (COCHN$_2$).

(ii) The diazoketone (10 mmol) in dry ethyl acetate (200 ml) was cooled to −15° C. and 1M HBr/ethyl acetate (about 11 ml) added dropwise. When the yellow colour was discharged TLC (ethyl acetate/hexane) showed complete conversion of the diazoketone to bromomethyl ketone. The solution was rapidly transferred to a separating funnel and washed with 1M KHCO$_3$, brine, dried and evaporated to leave a solid. Dissolution in hot EtOH and cooling gave the bromomethyl ketone as an amorphous white powder.

NMR (CDCl$_3$): δ1.3 (5, 9H), 1.5–1.85 (m, 4H), 3.75–3.95 (m+s, 4H), 4.3 (m, 1H), 5.05 (s, 2H), 5.15 (s, 2H), 5.65 (d, 2H), 7.30 (m, 10H), 9.2 (br, s, 1H), 9.3 (br, s, 1H). Melting point: Softens at 50° C. then slowly decomposed >70° C.

Boc-DCha-X-ONSu (X=Pro, Pic or Aze)

(i) Boc-DCha—OH (10 mmol) in CH$_2$Cl$_2$/DMF (1:5 50 ml) was treated with HONSu (11 mmol), cooled to 0° C. and WSCDI (13 mmol) added. After 30 min it was warmed to room temperature. TLC after 3 h showed complete formation of Boc-DCha-ONSu. Addition of Et$_2$O (200 ml) and washing with H$_2$O (3×), brine, drying gave the ester as a colourless foam.

(ii) The N-hydroxysuccinimido ester (10 mmol) in CH$_2$Cl$_2$ (50 ml) was treated with H-Pro-OBzl.HCl or H-Pic-OBzl.HCl or H-Aze-OBzl (11 mmol) and iPr$_2$-NEt (20 mmol). After stirring for 3 h, standard ethyl acetate/0.3M KHSO$_4$ work-up gave the dipeptide ester which was pure enough to be used in the next step.

(iii) The Boc-DCha-X-OBzl in THF was hydrogenated over 5% Pd/C at STP for 4 h. Filtration and evaporation gave the acid as a solid or foam. Re-crystallisation (iPr$_2$O or Et$_2$O/hexane) gave the pure products. Boc-DCha-Pro—OH (solid m.p. 163°–166° C.): NMR (CDCl$_3$) δ0.8–2.05 (m,+s at 1.4, 26H), 3.4 (m, 1H), 3.85 (m, 1H), 4.5 (m, 2H), 5.2 (m, 1H).

Boc-DCha-Pic—OH (solid m.p. 121°–122° C.): NMR (CDCl$_3$) δ0.8–2.05 (m,+s at 1.45, 28H), 3.35 (m, 1H), 3.95 (m, 1H), 4.6–4.9 (m, 1H), 5.4 (m, 1H), 5.6 (m, 1H), 8.8 (br, s, 1H).

Boc-(Me)DCha-Pro-ONSu

Boc-(Me)DPhe—OH was hydrogenated over 5% Rh-C in 90% acetic acid-H$_2$O at 0.41 MPa for 3 days giving quantitative yield of Boc-(Me)DCha—OH. Boc-(Me)DCha—OH (10 mmol) and NMM (10 mmol) in CH$_2$Cl$_2$ (50 ml) was cooled to −15° C. and Ph$_2$PO-Cl (10 mmol) added. After 20 min, H-Pro-OBzl.HCl (11 mmol) and NMM (20 mmol) was added. After 1 h it was allowed to warm to room temperature. After 2 h standard work-up and flash chromatography (40% ethyl acetate/hexane) gave pure Boc-(Me)DCha-Pro-OBzl as a colourless oil (80%).

NMR (CDCl₃): δ0.5–2.2 (m,+s at 1.4, 26H) 2.65 (s, 3H), 3.5 (m, 2H), 4.3–5.0 (m, 2H), 5.1 (s, 2H), 7.30 (s, 5H). This was converted into the N-hydroxysuccinimido ester as described for Boc-DCha-X-ONSu below.

Synthesis schemes:

Procedure (A)

Procedure (B)

Procedure (C)

Procedure (D)

Y = O, S
R⁴ = nBu, Aryl
For Example 1: R⁴YH = HO₂CCOPh

Procedure (E)

-continued
Synthesis schemes:

(iii)

e.g. $R^4$ = Me, Et, nPr, nBu
Then continue as in Procedure (A)

Procedure (F)

e.g. $R^4$ = $CH_2CF_3$, $CH_2(CF_2)_2CF_3$, Ph(4-OMe)
Then continue as in Procedure (A)

Procedure (G)

e.g. $R^4$ = $CH_2CF_3$

Procedure (H)

e.g. $R^4$ = $CH_2CF_3$

Preparation procedures:

The following preparation procedures illustrate the above methods I–III as well as subsequent steps to final compounds.

Procedure (A)

(i) Boc-Arg($Z_2$)—$CH_2Br$ (10 mmol) was added as a solid to a preformed solution of the alkoxide or phenoxide (alcohol or phenol 10 mmol and 80% NaH-oil, 10 mmol) in DMF (40 ml) at −20° C. under $N_2$. After 30 min the solution was warmed to room temperature. 2 hours later 0.3M $KHSO_4$ was added to neutralize any alkoxide remaining and the DMF removed under vacuum. The crude product was partitioned between ethyl acetate and $H_2O$, the ethyl acetate layer washed with brine, dried and evaporated. Flash chromatography or crystallisation gave the pure alkoxyketones.

Boc-Arg($Z_2$)—$CH_2OPh$ (solid): NMR ($CDCl_3$): δ1.41 (s, 10H), 1.64–1.68 (m, 3H), 3.92 (dd, 2H), 4.5 (m, 1H), 4.62 (q, 2H), 5.1 (s, 2H), 5.2 (s, 2H), 5.5 (d, 1H), 6.8 (d, 2H), 6.95 (t, 1H), 7.2–7.45 (m, 12H), 9.2 (br, s, 1H), 9.3 (br, s, 1H). Melting point 115°–118° C.

Boc-Arg($Z_2$)—$CH_2OCH_2CF_3$ (solid): NMR ($CDCl_3$): δ1.35 (s, 10H), 1.55–1.75 (m, 3H), 3.7 (q, 2H), 3.85 (m, 2H), 4.2 (q+m, 3H), 5.05 (s, 2H), 5.15 (s, 2H), 5.7 (d, 1H), 7.15–7.35 (m, 10H), 9.15 (br, s, 1H), 9.3 (br, s, 1H). Melting point 87°–90° C.

(ii) The alkoxymethyl or phenoxymethyl ketone in MeOH/THF (1:1) at 0° C. was treated with $NaBH_4$ (1 equiv.). After 10 min, 0.3M $KHSO_4$ was added to pH 7 and the mixture evaporated to remove MeOH/THF. Ethyl acetate was added and after standard work-up (ethyl acetate/0.3M $KHSO_4$) the alcohol was isolated as a diastereomeric mixture.

(iii) The alcohol was treated with 4M HCl in dioxan for 15 min at room temperature and evaporated. The residue in $CH_2Cl_2$ (1 mmol in 5 ml) was treated with Boc-DCha-X-ONSu (1 equiv.) and $iPr_2NEt$ (to pH 9 on wet pH paper). After 3 h, standard work-up gave the modified tripeptide which was purified by flash chromatography (ethyl acetate-hexane mixtures containing 1% acetic acid). Yield: 50–85%.

(iv) The tripeptide alcohol in $CH_2Cl_2$ was treated with Dess-Martin periodinane (3 equiv.) (Dess, D. B. and Martin, J. C. J. Org. Chem. 1983, 48. 4155–4156). After 2 h stirring at room temperature, standard work-up ($Et_2$/1M $KHCO_3$/$Na_2S_2O_3$) gave the crude tripeptide ketones which were purified by flash chromatography (ethyl acetate-hexane).

(v) The ketone was treated with 4M HCl-dioxan for 15 min at room temperature and evaporated. The residue in dry MeCN (1 mmol in 5 ml) was treated with benzylbromoacetate or tertiary butyl bromoacetate (1.2 equiv.) and $iPr_2NEt$ (3 equiv.). After reflux for 2 h the solution was evaporated and flash columned (ethyl acetate-hexane) giving the benzyloxycarbonylmethyl or tertiary butyloxycarbonylmethyl peptides as oils (40–50%).

In Examples 30 and 31, 2.5 equiv. of the bromoacetate were used to achieve bis-alkylation.

Procedure (B)

The peptide alkoxymethylketone was treated with excess 4M HCl-dioxan for 15 min at room temperature. Evaporation gave the HCl salt which was partitioned between ethyl acetate and 1M $KHCO_3$. The ethyl acetate was separated, dried and evaporated giving the free amine which was taken up in MeOH and freshly distilled tertiary butylacrylate added (1.5 equiv.). Reflux for 4 h gave the tertiary butoxycarbonylethyl peptide which was purified by flash chromatography in ethyl acetate/hexane.

Procedure (C)

Boc-Arg($Z_2$)—$CHN_2$ (1 mmol) dissolved in the alcohol. $R^4OH$ (5 ml) was treated with $Rh_2(OAc)_4$ (cat.). After several hours at room temperature, TLC analysis showed no diazoketone remaining. The alcohol was removed in vacuo and the product isolated by flash chromatography using ethyl acetate/hexane mixtures.

Procedure (D)

(i) Boc-Arg($Z_2$)—OH (10 mmol) in dry $CH_2Cl_2$ (50 ml) was treated with 2,2,2-trichloroethanol (11 mmol) and 4-DMAP (1 mmol), cooled to 0° C. and WSCDI (13 mmol) added. After 30 min, it was allowed to warm to room temperature and stirred for 24 h. Evaporation and partition between ethyl acetate/0.3M $KHSO_4$, followed by 3×washes with 0.3M $KHSO_4$, 1×$H_2O$, 1× brine, drying and evaporation gave the Tce ester which was used as such.

(ii) The Tce ester (10 mmol) was treated with 4M HCl—dioxan (50 ml) for 20 min at room temperature and then evaporated. After drying, the residue in $CH_2Cl_2$ (50 ml) was treated sequentially with Boc- DCha-X-ONSu (10 mmol) (X=Pro, Pic) and iPr₂NEt (to pH 9 on wet pH paper). After 3 h, standard work-up (ethyl acetate/0.3M KHSO₄) gave the tripeptide ester as an oil. The Tce ester (10 mmol) in 90% acetic acid-H₂O (50 ml) was treated at 5 min intervals with small portions of freshly activated Zn over 1 h. After a further 1 h, the mixture was filtered and the solution evaporated. Standard work-up (ethyl acetate/0.3M KHSO₄) gave the tripeptide acid which was purified by flash chromatography on silica (2% acetic acid-ethyl acetate) giving the tripeptide acid as a colourless foam (80% over 3 steps).

(iii) The tripeptide acid was converted into the bromomethyl ketone using the same procedure as that described for Boc-Arg(Z₂)—CH₂Br. The tripeptide bromomethyl ketone was obtained as a colourless oil by flash chromatography using ethyl acetate/hexane mixtures.

NMR (CDCl₃): δ0.9 (m), 1.15 (m), 1.25 (m), 1.35 (s), 1.6 (m), 1.85 (m), 2.1 (m) [total 30H], 3.3 (m, 1H), 3.7 (m, 1H), 3.95 (m, 2H), 4.15 (s, 2H), 4.25 (m, 1H), 4.4 (m, 1H), 4.5 (m, 1H), 5.0 (d, 1H), 5.1 (dd, 2H), 5.2 (s, 2H), 7.2–7.4 (s, m, 10H), 9.2–9.5 (2 br, s, 2H).

(iv) The tripeptide bromomethyl ketone (1 mmol) in dry DMF (5 ml) was treated with fluorinated alcohol, phenol or thiol (1.2 mmol) and anhydrous potassium fluoride (1.5 mmol) and stirred at room temperature for 24 h. Evaporation followed by standard work-up and flash chromatography gave the tripeptide ketones.

Boc-DCha-Pro-Arg(Z₂)—CH₂O-Ph(4-Me): NMR (CDCl₃) δ0.9 (m), 1.15 (m), 1.25 (m), 1.35 (s), 1.6 (m), 1.85 (m), 2.1 (m) [total 30H], 2.38 (s, 3H), 3.4 (m, 1H), 3.9 (m, 1H), 4.1 (br, s, 2H), 4.4 (m, 1H), 4.6 (m, 1H), 4.7 (m, 1H), 4.9 (q, 2H), 6.9 (d, 1H), 7.15 (d, 1H), 7.4–7.5 (m, 2H), 7.45 (s, 10H), 9.4 (br, s, 1H), 9.6 (br, s, 1H).

For Example 37 the protected sulphide was oxidised to the sulphone using m-chloroperbenzoic acid in dichloromethane at room temperature.

Procedure (E)

(i) Boc-Arg(Z₂)—CH₂Br (10 mmol) and benzoylformic acid (12 mmol) in DMF (40 ml) were treated with KF (14 mmol). After stirring for 3 h the DMF was evaporated and the product partitioned between ethyl acetate/H₂O. Drying and evaporation gave the crude benzoylformate ester which was purified by crystallisation (CH₂Cl₂-hexane) giving the product as a white solid (86%).

NMR (CDCl₃): δ1.4 (s, 9H), 1.65–1.9 (m, 4H), 3.95 (m, 2H), 4.3 (m, 1H), 4.95 (q, 2H), 5.15 (ABq, 2H), 5.25 (s, 2H), 5.9 (d, 1H), 7.35 (m, 10H), 7.5 (t, 2H), 7.65 (t, 1H), 8.15 (t, 2H), 9.25 (br, s, 1H), 9.45 (br, s, 1H). Melting point 130°–132° C.

(ii) The benzoylformate ester (5 mmol) in THF (200 ml) and 1M KHCO₃ (200 ml) was stirred vigorously at room temperature for 24 h. The THF was separated and evaporated and the aqueous phase extracted with ethyl acetate which was combined with the material from the THF. Crystallisation from CH₂Cl₂-hexane gave the α-ketol as a white solid (90%).

NMR (CDCl₃): δ1.4 (s, 9H), 1.7 (m, 4H), 2.95 (t, 1H), 3.95 (m, 2H), 4.25 (m, 2H), 5.15 (s, 2H), 5.25 (s, 2H), 5.6 (d, 1H), 7.35 (m, 10H), 9.25 (br, s, 1H), 9.4 (br, s, 1H). Melting point 101°–103° C.

(iii) The α-ketol (1 mmol) in dry CH₂Cl₂ (5 ml) was treated with alkyl iodide (5 to 10 mmol) and silver oxide (2 mmol). The mixture was refluxed in the dark for 2 to 17 hours (e.g. MeI, EtI, nPrI: 2 h; nBuI: 5 h). Evaporation followed by flash chromatography (ethyl acetate-hexane) gave the alkoxymethyl ketones as colourless oils (50–85%).

Boc-Arg(Z₂)—CH₂OEt (oil): NMR (CDCl₃): δ1.15 (t, 3H), 1.4 (s, 9H), 1.5–1.8 (m, 4H), 3.4 (q, 2H), 3.95 (t, 2H), 4.1 (q, 2H), 4.45 (m, 1H), 5.15 (s, 2H), 5.25 (s, 2H), 5.4 (d, 1H), 7.35 (m, 10H), 9.25 (br, s, 1H), 9.4 (br, s, 1H).

Boc-Arg(Z₂)—CH₂NBu (oil): NMR (CDCl): δ0.9 (t, 3H), 1.25–1.8 (m)+1.4 (s) [17H], 3.3 (dd, 2H), 3.95 (t,2H), 4.05 (q, 2H), 4.45 (m, 1H), 5.1 (s, 2H), 5.2 (s, 2H), 5.35 (d, 1H), 7.35 (m, 10H), 9.25 (br, s, 1H), 9.4 (br, s, 1H).

Procedure (F)

Boc-Arg(Z₂)—CH₂Br was treated with CF₃CH₂OH, CF₃(CF₂)₂CH₂OH or Ar—OH and KF in DMF using the procedure outlined in Procedure (D) (iv).

Procedure (G)

The Boc protected peptides were treated with 4M HCl-dioxan for 15 min at room temperature and evaporated. The residue in CH₂Cl₂ was treated with MeSO₂Cl (1.1 equiv.) and iPr₂NEt (2.5 equiv.). After 1 h standard work-up and flash-chromatography gave the methylsulphonylpeptides which were deprotected as in Deprotection procedure (a).

Procedure (H)

The peptides were Boc deprotected as above and the HCl washed out using ethyl acetate/1M KHCO₃ partition. The free amines in MeOH cooled to 0° C. were treated with the aldehyde Ch—CHO (1.5 equiv.) and NaCNBH₃ (1 equiv.). After 1 hour evaporation in the cold and flash chromatography gave the N-alkylated peptide. Deprotection using Deprotection procedure (a).

Procedure (I)

Boc-(3-trans-phenyl)-D,Lproline was prepared as described in Chung et al. J. Org. Chem. 1990, 55, 270, and coupled to H-Pro-OBzl as described above for Boc-(Me)DCha-Pro-OBzl. The dipeptide was then converted to its -ONSu ester as described below.

Boc-(3-trans-cyclohexyl)-D,Lproline was prepared from the phenyl analogue by hydrogenation over 5% Rh-C in 90% HOAc-H₂O at 0.41 MPa for 3 days.

Procedure (K)

Synthesis of the intermediate N-(BzlO₂C—CH₂—), N-(CF₃CO)—DCha-Pro-ONSu (i) Z-DCha-Pro-OtBu (made by standard peptide coupling reactions) was hydrogenated in THF over 5% Pd-C at standard temperature and pressure for 24 h. Filtration and evaporation provided H-DCha-Pro-OtBu (oil, 100%).

(ii) The previous product (2 mmol) and benzyl glyoxylate (1 equivalent) in benzene were subjected to three evaporations (fresh benzene added each time) to remove water. The residual imine (2 mmol) in 1% acetic acid/methanol (8 ml) was treated with NaCNBH₃ (2 mmol). After 1 h, evaporation followed by flash chromatography on silica (60% EtOAc-hexane) gave BzlO$_2$C—CH$_2$-DCha-Pro-OtBu, 385 mg (41%).

(iii) The above product (380 mg) in dry CH$_2$CL$_2$ (8 ml) was treated with Et$_3$N (2 equivalents) and (CF$_3$CO)$_2$O (1.2 equivalents). After 40 min, evaporation and flash chromatography (silica, 30% EtOAC-hexane) gave the N-(BzlO$_2$C—CH$_2$—), N-(CF$_3$CO)-DCha-Pro-OtBu as an oil, 390 mg (86%).

$^1$HNmr(COCl$_3$)—complex due to presence of 4 rotamers—e.g. tBu group at δ1,4–1.5 was split four times in the ratio 1:0.25:0.8:0.4. δ0,9(m), 1.1(m), 1.65(m), 1.95(m), 2.2(m) [17H]; 1.4–1.5 [4xs, 9H]; 3.1 (m), 3.5(m), 3.7(m) [2H]; 4.3–4.6 [m,3H]; 5.05–5.4 (m,3H); 7.35 [≈s,5H].

(iv) The above product (335 mg) was treated with CH$_2$CL$_2$-TFA (1:1,8 ml)for 2.5 h at room temperature. Evaporation followed by three evaporations from toluene gave the free acid, 100%.

(v) The previous acid was converted to its —ONSu ester (100%) using HONSu as described previously for Boc-DCha—OH.

The intermediate may be coupled to H-Arg(Z)$_2$—CH$_2$—Y—R$^4$ using the general methods already outlined. Deprotection procedure a provides the peptide protected with N—CF$_3$—CO—. The N—CF$_3$—CO is removed by deprotection procedure d.

Deprotection procedures:

(a) The protected peptide in MeOH/H$_2$O (3:1) containing 1M HCl (2 equivalents) was hydrogenated over 5% Pd/C at STP for 40 min. Filtration (0.2 μm) and evaporation was followed by lyophilization from water to give the peptides as fluffy white solids. Purification, if required, was carried out by MPLC (see general procedures).

(b) The protected peptide was first treated with TFA/CH$_2$Cl$_2$ (1:1) for 1 hour and evaporated, then hydrogenated as above under (a).

(c) The COCOPh group was first hydrolysed as in (E) (ii) then hydrogenated over H$_2$-Pd/C as in (a).

(d) Removal of N—CF$_3$—CO (N-trifluoroacetyl):

The N-trifluoroacetyl peptide was dissolved in MeCN—H$_2$O—0.880 ammonia (1:1:1) and kept at room temperature for 24 h. Evaporation followed by purification if necessary provided the peptide.

EXAMPLES

The following examples illustrates the principles of the invention in more detail.

Examples of compounds of the invention are listed in Table 1, Table 2 indicates the procedures used in their preparation and described in the section titled "Preparation procedures", and Table 3 presents characterising data for the compounds listed.

Examples 1–37

TABLE 1

| Example No. | Formula |
|---|---|
| 1 | H—DCha—Pro—D,LArg—CH$_2$—OH |
| 2 | H—DCha—Pro—D,LArg—CH$_2$—O—Me |
| 3 | H—DCha—Pro—Arg—CH$_2$—O—CH$_2$—CF$_3$ |
| 4 | H—DCha—Pro—Arg—CH$_2$—O—CH(CF$_3$)$_2$ |
| 5 | H—DCha—Pro—Arg—CH$_2$—O—C*H(Ph)—CF$_3$ |
| 6 | HOOC—CH$_2$—DCha—Pro—D,LArg—CH$_2$—O—CH$_2$—CF$_3$ |
| 7 | Et—OOC—CH$_2$—DCha—Pro—D,LArg—CH$_2$—O—CH$_2$—CF$_3$ |
| 8 | HOOC—CH$_2$—DCha—Pro—D,LArg—CH$_2$—O—CH$_2$—CF$_2$—CF$_2$—CF$_3$ |
| 9 | HOOC—CH$_2$—DCha—Pro—Arg—CH$_2$—O—Ph |
| 10 | HOOC—CH$_2$—DCha—Pro—D,LArg—CH$_2$—O—Ph(4-OMe) |
| 11 | HOOC—CH$_2$—DCha—Pro—D,LArg—CH$_2$—O—Ph(4-tBu) |
| 12 | HOOC—CH$_2$—DCha—Pro—D,LArg—CH$_2$—O—Ph(4-Me) |
| 13 | HOOC—CH$_2$—DCha—Pro—D,LArg—CH$_2$—O—Ph(4-F) |
| 14 | HOOC—CH$_2$—DCha—Pro—D,LArg—CH$_2$—O—Ph(3-F) |
| 15 | HOOC—CH$_2$—DCha—Pro—D,LArg—CH$_2$—O—Ph(2-F) |
| 16 | HOOC—CH$_2$—DCha—Pro—D,LArg—CH$_2$—O—Ph(3-CF$_3$) |
| 17 | HOOC—CH$_2$—DCha—Pro—D,LArg—CH$_2$—O—Ph(4-CF$_3$) |
| 18 | HOOC—CH$_2$—DCha—Pro—D,LArg—CH$_2$—O—Ph(2-CF$_3$) |
| 19 | HOOC—CH$_2$—DCha—Pro—D,LArg—CH$_2$—O—C$_6$F$_5$ |
| 20 | HOOC—CH$_2$—DCha—Pro—D,LArg—CH$_2$—O—Et |
| 21 | HOOC—CH$_2$—DCha—Pro—Arg—CH$_2$—O—nPr |
| 22 | HOOC—CH$_2$—DCha—Pro—Arg—CH$_2$—O—nBu |
| 23 | HOOC—CH$_2$—DCha—Pro—Arg—CH$_2$—O—iBu |
| 24 | HOOC—CH$_2$—DCha—Aze—D,LArg—CH$_2$—O—CH$_2$—CF$_3$ |
| 25 | HOOC—CH$_2$—DCha—Pic—D,LArg—CH$_2$—O—CH$_2$—CF$_3$ |
| 26 | HOOC—CH$_2$—DCha—Pic—Arg—CH$_2$—O—nBu |
| 27 | Me—DCha—Pro—D,LArg—CH$_2$—O—CH$_2$—CF$_3$ |
| 28 | Me—SO$_2$—DCha—Pro—D,LArg—CH$_2$—O—CH$_2$—CF$_3$ |
| 29 | Ch—CH$_2$—DCha—Pro—D,LArg—CH$_2$—O—CH$_2$—CF$_3$ |
| 30 | (HOOC—CH$_2$)$_2$—DCha—Pro—D,LArg—CH$_2$—O—CH$_2$—CF$_3$ |
| 31 | (HOOC—CH$_2$)$_2$—DCha—Pro—Arg—CH$_2$—O—iBu |
| 32 | HOOC—CH$_2$—CH$_2$—DCha—Pro—D,LArg—CH$_2$—O—nBu |
| 33 | HOOC—CH$_2$—CH$_2$—DCha—Pro—Arg—CH$_2$—O—CH$_2$—CF$_3$ |
| 34 | H—D,LPro(3-trans-Ph)—Pro—D,LArg—CH$_2$—O—CH$_2$— |
| 35 | H—D,LPro(3-trans-Ch)—Pro—D,LArg—CH$_2$—O—CH$_2$—CF$_3$ |
| 36 | HOOC—CH$_2$—DCha—Pro—Arg—CH$_2$—S—nBu |
| 37 | HOOC—CH$_2$—DCha—Pro—D,LArg—CH$_2$—SO$_2$—nBu |

*absolute configuration R or S

TABLE 2

| Example No. | Preparation procedure | Deprotection procedure |
|---|---|---|
| 1 | D | c |
| 2 | E | b |
| 3 | A or C | b |
| 4 | A or C | b |
| 5 | A or C | b |
| 6 | A | a |
| 7 | A | a |

TABLE 2-continued

| Example No. | Preparation procedure | Deprotection procedure |
|---|---|---|
| 8 | F | a |
| 9 | A or D | a |
| 10 | F | a |
| 11 | D | a |
| 12 | D | a |
| 13 | D | a |
| 14 | D | a |
| 15 | D | a |
| 16 | D | a |
| 17 | D | a |
| 18 | D | a |
| 19 | D | a |
| 20 | E | a |
| 21 | E | a |
| 22 | E | a |
| 23 | E | a |
| 24 | A | a |
| 25 | A | a |
| 26 | E | a |
| 27 | A and F | a |
| 28 | A and G | a |
| 29 | A and H | a |
| 30 | A | a |
| 31 | E | a |
| 32 | E and B | b |
| 33 | A and B | b |
| 34 | I and A | b |
| 35 | I and A | b |
| 36 | D | a |
| 37 | D | a |

TABLE 3

| Example No. | Mol. Wt | FAB MS (M + 1) | AAA: Peptide Content (%)* | HPLC retention** Time (min)/system |
|---|---|---|---|---|
| 1 | 438.57 | 439 | 56/Pro | 10.3/E |
| 2 | 452.60 | 453 | 65/Pro | 9.9/E |
| 3 | 520.6 | 521 | 59/Pro | 8.6/A |
| 4 | 588.6 | 589 | 60/Pro | 10.7/A |
| 5 | 596.7 | 597 | 61/Pro | 12.2/A |
| 6 | 578.64 | 579 | 72/Pro | 14.8/C |
| 7 | 606.69 | 607.7 | 65/Pro | 22.0/B |
| 8 | 678.65 | 679.8 | 76/Pro | 18.2/G |
| 9 | 572.71 | 573.3 | 73/Pro | 19.9/B |
| 10 | 602.74 | 603.8 | 76/Pro | 13.4/G |
| 11 | 628.82 | 629.5 | 77/Pro | 22.0/G |
| 12 | 586.74 | 587.2 | 75/Pro | 16.0/G |
| 13 | 590.70 | 591.4 | 76/Pro | 15.2/G |
| 14 | 590.70 | 591.4 | 63/Pro | 15.0/G |
| 15 | 590.70 | 591.4 | 54/Pro | 14.0/G |
| 16 | 640.71 | 641.5 | 68/Pro | 19.0/G |
| 17 | 640.71 | 641.6 | 70/Pro | 20.0/G |
| 18 | 640.71 | 641.4 | 65/Pro | 18.4/G |
| 19 | 662.66 | 663 | 49/Pro | 21.0/G |
| 20 | 524.67 | 525.4 | 79/Pro | 15.5/B |
| 21 | 538.69 | 539 | 67/Pro | 9.2/F |
| 22 | 552.72 | 553 | 69/Pro | 19.3/B |
| 23 | 552.72 | 553.4 | 56/Pro | 9.2/F |
| 24 | 564.61 | 565 | 67/Aze | 13.6/D |
| 25 | 592.66 | 593 | 90/Pic | 8.4/D |
| 26 | 566.75 | 567.4 | 86/Pic | 17.0/G |
| 27 | 534.63 | 535.6 | 70/Pro | 18.8/B |
| 28 | 598.69 | 599 | 71/Pro | 11.2/D |
| 29 | 616.77 | 617 | 64/Pro | 14.5/C |
| 30 | 636.67 | 637.6 | 70/Pro | 12.0/A |
| 31 | 610.76 | 611.2 | 67/Pro | 10.0/F |
| 32 | 566.75 | 567.5 | 65/Pro | 19.7/B |
| 33 | 592.66 | 593 | 46/Pro | 10.6/F |
| 34 | 540.59 | 541 | 56/Pro | 14.3/C |
| 35 | 546.64 | 547 | 49/Pro | 15.9/C |
| 36 | 568.78 | 569.4 | 45/Pro | 17.4/G |
| 37 | 600.78 | 601.3 | 62/Pro | 14.6/G |

*Based on amino acid as indicated
**See General experimental procedures. Times are given for L—Arg epimers. D-epimers (minor) usually run about 0.5 min earlier.
System A: 20% increased to 80% of 1% TFA—MeCN into 1% TFA—H$_2$O over 25 min. (20–80%, 25 min)
System B: 10–60%, 30 min
System C: 10–90%, 30 min
System D: 30–100%, 30 min
System E: 10–90%, 20 min
System F: 20–100%, 20 min
System G: 20–70%, 30 min

Example 38

Solution for continuous intravenous administration.
A solution is prepared from the following ingredients:

| | |
|---|---|
| Thrombin inhibitor | 50 mg |
| Sodium chloride for injection | 4.5 g |
| Water for injection up to 500 ml | |

The active constituent and the sodium chloride are dissolved in the water whereafter the solution is filtered and then sterilised by autoclaving or by filtration through a sterile 0.2 μm filter and aseptically filled into sterile infusion bottles.

Example 39

Solution for injection.
A solution is prepared from the following ingredients:

| | |
|---|---|
| Thrombin inhibitor | 5 g |
| Sodium chloride for injection | 9 g |
| Water for inj. up to 1000 ml | |

The active constituent and the sodium chloride are dissolved in the water whereafter the solution is filtered and then sterilised by autoclaving or by filtration through a sterile 0.2 μm filter and aseptically filled into sterile ampoules (5 ml).

Example 40

Solution for nasal administration
A solution is prepared from the following ingredients:

| | |
|---|---|
| Thrombin inhibitor | 10 g |
| Glycerol | 200 g |
| Methyl p-hydroxybenzoate | 1 g |
| Propyl p-hydroxybenzoate | 0.2 g |
| Water for inj. up to 1000 ml | |

The active constituent and the preservatives were dissolved in glycerol and the main part of the water. The volume is then adjusted to 1000 ml and the solution is filled into sterile polyethylene containers.

Example 41

Tablets for oral administration
1000 tablets are prepared from the following ingredients:

| Thrombin inhibitor | 100 g |
|---|---|
| Lactose | 200 g |
| Polyvinyl pyrrolidone | 30 g |
| Microcrystalline cellulose | 30 g |
| Magnesium stearate | 6 g |

The active constituent and lactose are mixed with an aqueous solution of polyvinyl pyrrolidone. The mixture is dried and milled to form granules. The microcrystalline cellulose and then the magnesium stearate are then admixed. The mixture is then compressed in a tablet machine giving 1000 tablets, each containing 100 mg of active constituent.

Example 42

Gelatine capsules for oral administration

Gelatine capsules are filled with a mixture of the following ingredients:

| Thrombin inhibitor | 50 mg |
|---|---|
| Magnesium stearate | 3 mg |
| Lactose | 100 mg |

BIOLOGY

Determination of thrombin clotting time and $IC_{50}TT$:

Human thrombin (T 6769, Sigma Chem Co) in buffer solution, pH 7.4, 100 μl, and inhibitor solution, 100 μl, are incubated for one min. Pooled normal citrated human plasma, 100 μl, is then added and the clotting time measured in an automatic device (KC 10, Amelung).

The clotting time in seconds is plotted against the inhibitor concentration, and the $IC_{50}TT$ is determined by interpolation.

$IC_{50}TT$ is the concentration of inhibitor that doubles the thrombin clotting time for human plasma. $pIC_{50}TT$ is the −log 10 of $IC_{50}TT$ in mol/l. The results are presented in Table 4.

TABLE 4

| Example No. | $pIC_{50}TT$ |
|---|---|
| 1 | 7.71 |
| 2 | 7.81 |
| 3 | 7.92 |
| 4 | 7.38 |
| 5 | 7.77 |
| 6 | 8.04 |
| 7 | 7.70 |
| 8 | 7.64 |
| 9 | 8.45 |
| 10 | 7.90 |
| 11 | 7.86 |
| 12 | 8.25 |
| 13 | 8.22 |
| 14 | 8.15 |
| 15 | 8.12 |
| 16 | 7.77 |
| 17 | 8.68 |
| 18 | 7.30 |

TABLE 4-continued

| Example No. | $pIC_{50}TT$ |
|---|---|
| 19 | 8.27 |
| 20 | 8.17 |
| 21 | 8.14 |
| 22 | 8.69 |
| 23 | 7.64 |
| 24 | 8.01 |
| 25 | 8.00 |
| 26 | 7.89 |
| 27 | 7.52 |
| 28 | 6.85 |
| 29 | 6.47 |
| 30 | 7.38 |
| 31 | 6.88 |
| 32 | 7.63 |
| 33 | 7.78 |
| 34 | 7.03 |
| 35 | 7.25 |
| 36 | 7.57 |
| 37 | 7.72 |

ABBREVIATIONS

| | |
|---|---|
| 4-DMAP = | 4-dimethylamino pyridine |
| AAA = | amino acid analysis |
| Arg = | L-arginine |
| Arg($Z_2$) = | δN, ωN-dibenzyloxycarbonyl-L-arginine |
| Aze = | L-azetidine-2-carboxylic acid |
| Boc = | tertiary butoxy carbonyl |
| Bu = | butyl |
| Bzl = | benzyl |
| Ch = | cyclohexyl |
| Cha = | L-β-cyclohexylalanine |
| DMF = | dimethyl formamide |
| Et = | ethyl |
| EtOAc = | ethyl acetate |
| FAB = | fast atom bombardment |
| FI to FXIII = | coagulation factors I to XIII |
| $FII_a$ to $FXIII_a$ = | activated form of coagulation factors II to XIII |
| Gly = | glycine |
| HMW-K = | high molecular weight kininogen |
| HOAc = | acetic acid |
| HONSu = | N-hydroxysuccinimide |
| HPLC = | high performance liquid chromatography |
| iBC = | isobutyl chloroformate |
| Kall = | kallikrein |
| Me = | methyl |
| MPLC = | medium pressure liquid chromatography |
| NMM = | N-methyl morpholine |
| Nph = | naphthyl |
| Ph = | phenyl |
| Pic = | L-pipecolinic acid |
| PL = | phospholipids |
| Pr = | propyl |
| Prekall = | prekallikrein |
| Pro = | L-proline |
| STP = | standard temperature and pressure |
| Tce = | 2,2,2-trichloroethyl |
| TFA = | trifluoracetic acid |
| THF = | tetrahydrofuran |
| Val = | L-valine |
| WSCDI = | water soluble carbodiimide |
| Z = | benzyloxy carbonyl |

Prefixes n, i and t have their usual meanings: normal, iso and tertiary.

We claim
1. A compound of the general formula

(1)

wherein:
A represents —CH$_2$—, —CH=CH—, —CH$_2$—CH$_2$— or —CH$_2$—CH$_2$—CH$_2$—;
R$^1$ and R$^2$ are the same or different and each represents H or X-B-, where B is a straight or branched alkylene group having 1–3 carbon atoms and X is H, methyl, ethyl, a cycloalkyl group having 3–6 carbon atoms or R'CO—, where R' is OH, a straight or branched alkoxy group having 1–4 carbon atoms, NH$_2$ or NHR", where R" is a straight or branched alkyl group having 1–4 carbon atoms; or X is a carboxylic acid selected from the group consisting of —PO(OR''')$_2$'—SO$_3$H and 5-(1H)tetrazolyl, wherein R''' is H, methyl or ethyl; or B is —SO$_2$— and X is methyl or ethyl;
m is 0, 1 or 2, and R$^3$ represents a cyclohexyl group and R$^{3,4}$ represents H; or m is 1 and R$^3$ represents a cyclohexyl or phenyl group and R$^{3,4}$ forms an ethylene bridge together with R$^1$;
Y represents O or S(O)p, where p is 0, 1 or 2;
R$^4$ represents H, a straight or branched alkyl or a cycloalkyl having 1 to 6 carbon atoms unsubstituted or substituted with one or more fluoro atoms or substituted with a phenyl group or both; a substituted or unsubstituted aromatic ring selected from the group consisting of phenyl, 4-methoxy-phenyl, 4-tertiary-butyl-phenyl, 4-methyl-phenyl, 2-, 3- or 4-trifluoro-methyl-phenyl, and phenyl substituted with 1–5 fluoro atoms;
or —CH(CF$_3$)-phenyl, either as such or in the form of a physiologically acceptable salt or a stereoisomer thereof.

2. A compound according to claim 1 wherein
A represents —CH$_2$—CH$_2$— or —CH$_2$—CH$_2$—CH$_2$—;
R$^1$ is H and R$^2$ represents HOCO(CH$_2$)$_n$— or CH$_3$CH$_2$OCO(CH$_2$)$_n$—, and n is 1 or 2;
Y is O
m is 1, R$^3$ represents a cyclohexyl group and R$^{3,4}$ represents H.

3. A compound selected from the group consisting of
H-DCha-Pro-Arg-CH$_2$—OH,
H-DCha-Pro-Arg-CH$_2$—O-Me,
H-DCha-Pro-Arg-CH$_2$—O—CH$_2$—CF$_3$,
H-DCha-Pro-Arg-CH$_2$—O—CH(CF$_3$)$_2$,
H-DCha-Pro-Arg-CH$_2$—O—(R or S)CH(Ph)—CF$_3$,
HOOC—CH$_2$-DCha-Pro-Arg-CH$_2$—O—CH$_2$—CF$_3$,
Et-OOC—CH$_2$-DCha-Pro-Arg-CH$_2$—O—CH$_2$—CF$_3$,
HOOC—CH$_2$-DCha-Pro-Arg-CH$_2$—O—CH$_2$—CF$_2$—CF$_3$,
HOOC—CH$_2$-DCha-Pro-Arg-CH$_2$—O-Ph,
HOOC—CH$_2$-DCha-Pro-Arg-CH$_2$—O-Ph(4-OMe),
HOOC—CH$_2$-DCha-Pro-Arg-CH$_2$—O-Ph(4-tBu),
HOOC—CH$_2$-DCha-Pro-Arg-CH$_2$—O-Ph(4-Me),
HOOC—CH$_2$-DCha-Pro-Arg-CH$_2$—O-Ph(4-F),
HOOC—CH$_2$-DCha-Pro-Arg-CH$_2$—O-Ph(3-F),
HOOC—CH$_2$-DCha-Pro-Arg-CH$_2$—O-Ph(2-F),
HOOC—CH$_2$-DCha-Pro-Arg-CH$_2$—O-Ph(3-CF$_3$),
HOOC—CH$_2$-DCha-Pro-Arg-CH$_2$—O-Ph(4-CF$_3$), HOOC—CH₂-DCha-Pro-Arg-CH₂—O-Ph(2-CF₃),
HOOC—CH₂-DCha-Pro-Arg-CH₂—O—C6F5,
HOOC—CH₂-DCha-Pro-Arg-CH₂—O-Et,
HOOC—CH₂-DCha-Pro-Arg-CH₂—O-nPr,
HOOC—CH₂-DCha-Pro-Arg-CH₂—O-nBu,
HOOC—CH₂-DCha-Pro-Arg-CH₂—O-iBu,
HOOC—CH₂-DCha-Aze-Arg-CH₂—O—CH₂—CF₃,
HOOC—CH₂-DCha-Pic-Arg-CH₂—O—CH₂—CF₃,
HOOC—CH₂-DCha-Pic-Arg-CH₂—O-nBu,
Me-DCha-Pro-Arg-CH₂—O—CH₂—CF₃,
Me-SO2-DCha-Pro-Arg-CH₂—O—CH₂—CF₃,
Ch—CH₂-DCha-Pro-Arg-CH₂—O—CH₂—CF₃,
(HOOC—CH₂)₂-DCha-Pro-Arg-CH₂—O—CH₂—CF₃,
(HOOC—CH₂)₂-DCha-Pro-Arg-CH₂—O-iBu,
HOOC—CH₂—CH₂-DCha-Pro-Arg-CH₂—O-nBu,
HOOC—CH₂—CH₂-DCha-Pro-Arg-CH₂—O—CH₂—CF₃,
H-D  -Pro(3-trans-Ph)-Pro-Arg-CH₂—O—CH₂—CF₃,
H-D  Pro(3-trans-Ch)-Pro-Arg-CH₂—O—CH₂—CF₃,
HOOC—CH₂-DCha-Pro-Arg-CH₂—S-nBu and
HOOC—CH₂-DCha-Pro-Arg-CH₂—SO2-nBu,
either as such or in the form of a physiologically acceptable salt or stereoisomers thereof.

4. A method for obtaining inhibition of thrombin in a mammalian organism in need of such inhibition, comprising administering to said organism an inhibitory effective amount of a compound claimed in any one of claims 1–3.

5. A method of treatment or prophylaxis of thrombosis and hypercoagulability in blood and tissues in a mammalian organism, comprising administering to a host in need of such treatment or prophylaxis an effective amount of a compound claimed in any one of claims 1–3.

6. A compound of the formula, HOOC—CH₂-DCha-Pro-Arg-CH₂—O—CH₂—CF₃, or a physiologically acceptable salt or a stereoisomer thereof.

7. A compound of the formula, HOOC—CH₂-DCha-Pic-Arg-CH₂—O—CH₂—CF₃, or a physiologically acceptable salt or a stereoisomer thereof.

8. A compound of the formula, HOOC—CH₂-DCha-Pic-Arg-CH₂—O-nBu, or a physiologically acceptable salt or a stereoisomer thereof.

9. A compound of the formula, HOOC—CH₂—CH₂-DCha-Pro-Arg-CH₂—O-nBu, or a physiologically acceptable salt or a stereoisomer thereof.

10. A compound of the formula, HOOC—CH₂—CH₂-DCHa-Pro-Arg-CH₂—O—CH₂.CF₃, or a physiologically acceptable salt or a stereoisomer thereof.

11. A compound of the formula, HOOC—CH₂-DCHA-Pro-Arg-CH₂—O-nBu, or a physiologically acceptable salt or a stereoisomer thereof.

12. A pharmaceutical composition comprising a therapeutically effective amount of a compound according to any one of claims 1, 2, 3, 6, 7, 8, 9, 10, and 11 in a pharmaceutically acceptable carrier.

13. The method of claim 4 wherein the inhibitory effective amount is 1–1000 mg of active ingredient.

14. The method of claim 5 wherein the effective unit dosage amount of the compound is 1–1000 mg.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (iii) HYPOTHETICAL: NO (v) FRAGMENT TYPE: N-terminal (vi) ORIGINAL SOURCE:
    (A) ORGANISM: Homo sapiens (ix) FEATURE:
    (A) NAME/KEY: Peptide
    (B) LOCATION: 1..20
    (D) OTHER INFORMATION: /note="Peptide sequence containing
        thrombin cleavage site in the human fibrinogen
        A-alpha chain."

(ix) FEATURE:
    (A) NAME/KEY: Cleavage-site
    (B) LOCATION: 16..17

(xi) SEQUENCE DESCRIPTION: SEQ ID NO:1:

Ala Asp Ser Gly Glu Gly Asp Phe Leu Ala Glu Gly Gly Gly Val Arg
1               5                   10                  15

Gly Pro Arg Val
        20